(12) United States Patent
Province et al.

(10) Patent No.: US 7,181,282 B1
(45) Date of Patent: Feb. 20, 2007

(54) IMPLANTABLE CARDIAC DEVICE WITH PVC DENSITY MONITORING, AND THERAPY CONTROL AND METHOD

(75) Inventors: Rose A. Province, San Jose, CA (US); Yelena Nabutovsky, Sunnyvale, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 381 days.

(21) Appl. No.: 10/868,272

(22) Filed: Jun. 14, 2004

(51) Int. Cl.
*A61N 1/365* (2006.01)

(52) U.S. Cl. .............. 607/17; 607/14; 607/25; 600/508; 600/509; 600/515

(58) Field of Classification Search ........... 607/14, 607/17, 25; 600/508, 509, 515
See application file for complete search history.

(56) References Cited

U.S. PATENT DOCUMENTS

| | | | | |
|---|---|---|---|---|
| 5,215,098 A | * | 6/1993 | Steinhaus et al. | 600/515 |
| 5,312,451 A | * | 5/1994 | Limousin et al. | 607/15 |
| 5,772,691 A | * | 6/1998 | Routh et al. | 607/9 |
| 5,978,711 A | * | 11/1999 | van Hove | 607/17 |
| 6,185,459 B1 | * | 2/2001 | Mehra et al. | 607/14 |
| 6,408,209 B1 | * | 6/2002 | Bouhour et al. | 607/19 |
| 6,516,219 B1 | | 2/2003 | Street | 600/515 |
| 2001/0007948 A1 | * | 7/2001 | Stoop et al. | 607/14 |
| 2002/0183636 A1 | | 12/2002 | Struble | 600/510 |

FOREIGN PATENT DOCUMENTS

| | | | |
|---|---|---|---|
| EP | 1 197 243 A2 | | 4/2002 |
| EP | 1 197 243 A3 | | 10/2003 |
| WO | WO 02/36001 A1 | * | 10/2002 |
| WO | WO 02/087695 A1 | | 11/2002 |
| WO | WO 03/057034 A1 | | 7/2003 |

* cited by examiner

*Primary Examiner*—Robert E. Pezzuto
*Assistant Examiner*—Erik J Bustamante
(74) *Attorney, Agent, or Firm*—Steven M. Mitchell

(57) ABSTRACT

An implantable cardiac device provides a learned premature ventricular contraction density function responsive to detected premature ventricular contractions. A current premature ventricular contraction density is then compared to the learned premature ventricular contraction density function to derive an indication of a condition of a heart and/or to control therapy administered to the heart.

28 Claims, 8 Drawing Sheets

IMPLANTABLE CARDIAC DEVICE WITH PVC DENSITY MONITORING, AND THERAPY CONTROL AND METHOD

FIELD OF THE INVENTION

The present invention generally relates to an implantable cardiac device and method that monitors PVC density. The present invention more particularly relates to such a device and method that provides a learned PVC density function which is used to assess patient condition and control appropriate therapy.

BACKGROUND OF THE INVENTION

Implantable cardiac devices are well known in the art. An implantable cardiac device may take the form of an implantable defibrillator (ICD) which treats accelerated rhythms of the heart such as fibrillation or an implantable pacemaker which maintains the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

For defibrillation, one lead may include at least one defibrillation electrode arranged to be positioned in the right ventricle. The ICD includes an arrhythmia detector that detects for ventricular arrhythmias, such as ventricular fibrillation. When such an arrhythmia is detected, a pulse generator delivers a defibrillating shock from the defibrillation electrode in the right ventricle to the device conductive housing to terminate the arrhythmia. Alternatively, such arrhythmia terminating systems may further include another defibrillation electrode arranged to be positioned in the right atrium and electrically connected to the right ventricular defibrillation electrode. In this arrangement, the defibrillating shock is delivered from the parallel connected right ventricular and right atrial electrodes to the conductive housing.

Ventricular fibrillation is an immediately life threatening cardiac arrhythmia. It requires immediate and effective defibrillation therapy.

However, it is best to prevent ventricular fibrillation from even occurring to avoid the need for defibrillation therapy and more importantly, to prevent exposure of the patient to such a life threatening arrhythmia. Premature ventricular contractions are believed to be an initial cause of ventricular fibrillation in some patients. A premature ventricular contraction (PVC) is a spontaneous (intrinsic) ventricular event that is not preceded by a paced or sensed atrial event. In patients who have previously suffered myocardia infarcts or ischemia, PVC's are considered particularly troublesome because they can trigger ventricular fibrillation or an accelerated ventricular arrhythmia, such as ventricular tachycardia, which may then accelerate the heart into fibrillation.

In view of the above, it is generally considered best to attempt to prevent or at least minimize the occurrence of PVCs in a patient's heart. Therapies such as overdrive pacing and vagal nervous system stimulation are known to treat the occurrence of PVCs.

The administration of PVC therapy to a heart requires detection of PVCs in a useful way which both indicates the condition of the patient's heart and when PVC therapy is required if not currently in use or when increased PVC therapy aggressiveness is required if such therapy is already enabled.

The monitoring of PVC density has been investigated as such a measure. PVC density is the number of PVCs detected during a preset period of time. PVC density variability has also been investigated as a possible measure. It has been found that patients with malignant ventricular arrhythmias have striking diurnal (daily) cycles in PVC density. Moreover, such studies indicate that patients at risk for ventricular arrhythmias may have more PVC density variability than those without such risk. Unfortunately, it has also been demonstrated that there are substantial day to day natural variations in ectopic variability. As a result, it would be difficult to prove a meaningful change in PVC density simply using overall daily PVC burden or random hourly PVC density monitoring. A more sensitive and accurate monitoring method is required to assess patient ventricular arrhythmia risk and to provide more effective PVC therapy control.

SUMMARY OF THE INVENTION

The invention provides an implantable cardiac device comprising a sensor that acquires a plurality of intracardiac electrograms from a heart, at least some of the electrograms including a premature ventricular contraction, and a detector that detects the premature ventricular contractions in the electrograms. The device further comprises a processor that provides a premature ventricular contraction density function responsive to the detected premature ventricular contractions, and an analyzer that derives an indication of a condition of the heart responsive to the premature ventricular contraction density function.

The premature ventricular contraction density function may be a diurnal premature ventricular contraction density function. The processor preferably averages a plurality of premature ventricular contraction density functions to provide a learned premature ventricular contraction density function, and the analyzer preferably compares the learned premature ventricular contraction density function to a current premature ventricular contraction density function to assess the condition of the heart or provide therapy control. The monitored condition may be premature ventricular contraction burden or electrical stability of the heart.

The processor may average a plurality of premature ventricular contraction density functions to provide a learned premature ventricular contraction density function. The processor may then determine a time varying premature ventricular contraction density threshold related to the learned premature ventricular contraction density function. A current premature ventricular contraction density may then be compared to the time varying premature ventricular contraction density threshold. This will enable, for example, premature ventricular contraction therapy control responsive to the comparison of the current premature ventricular contraction density to the time varying threshold.

The device may further include a pulse generator that provides stimulation pulses to the heart at a stimulation rate. The processor may average a plurality of premature ventricular contraction density functions to provide a learned premature ventricular contraction density function for each one of a plurality of different stimulate rates. A stimulation rate may then be selected responsive to the learned premature ventricular contraction density functions. The stimulation rate selected may be a rate corresponding to a learned premature ventricular contraction density function having a least premature ventricular contraction density function metric such as, for example, least total daily premature ventricular contraction density, least maximum premature ventricular contraction density, or least premature ventricular contraction density variability. The device may further include a premature ventricular contraction therapy circuit including a pulse generator that is enabled or controlled responsive to a change in the premature ventricular contraction density function metric.

The premature ventricular contraction therapy circuit may provide regular premature ventricular contraction therapy based upon the premature ventricular contraction density function.

The detector may also detect premature ventricular contraction complexes and the therapy circuit may provide therapy responsive to detection of a premature ventricular contraction complex density above a predetermined density. The premature ventricular contraction complexes may include at least one of premature ventricular contraction couplets, and premature ventricular contraction triplets.

The processor may further provide a density function of at least one of premature ventricular contraction couplets, premature ventricular contraction triplets, and premature ventricular contractions with coupling intervals less than a predetermined coupling interval.

The invention further provides a method comprising acquiring a plurality of intracardiac electrograms from a heart, at least some of the electrograms including a premature ventricular contraction, detecting premature ventricular contractions in the electrograms, providing a premature ventricular contraction density function responsive to the detected premature ventricular contractions, and deriving an indication of a condition of the heart responsive to the premature ventricular contraction density function.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
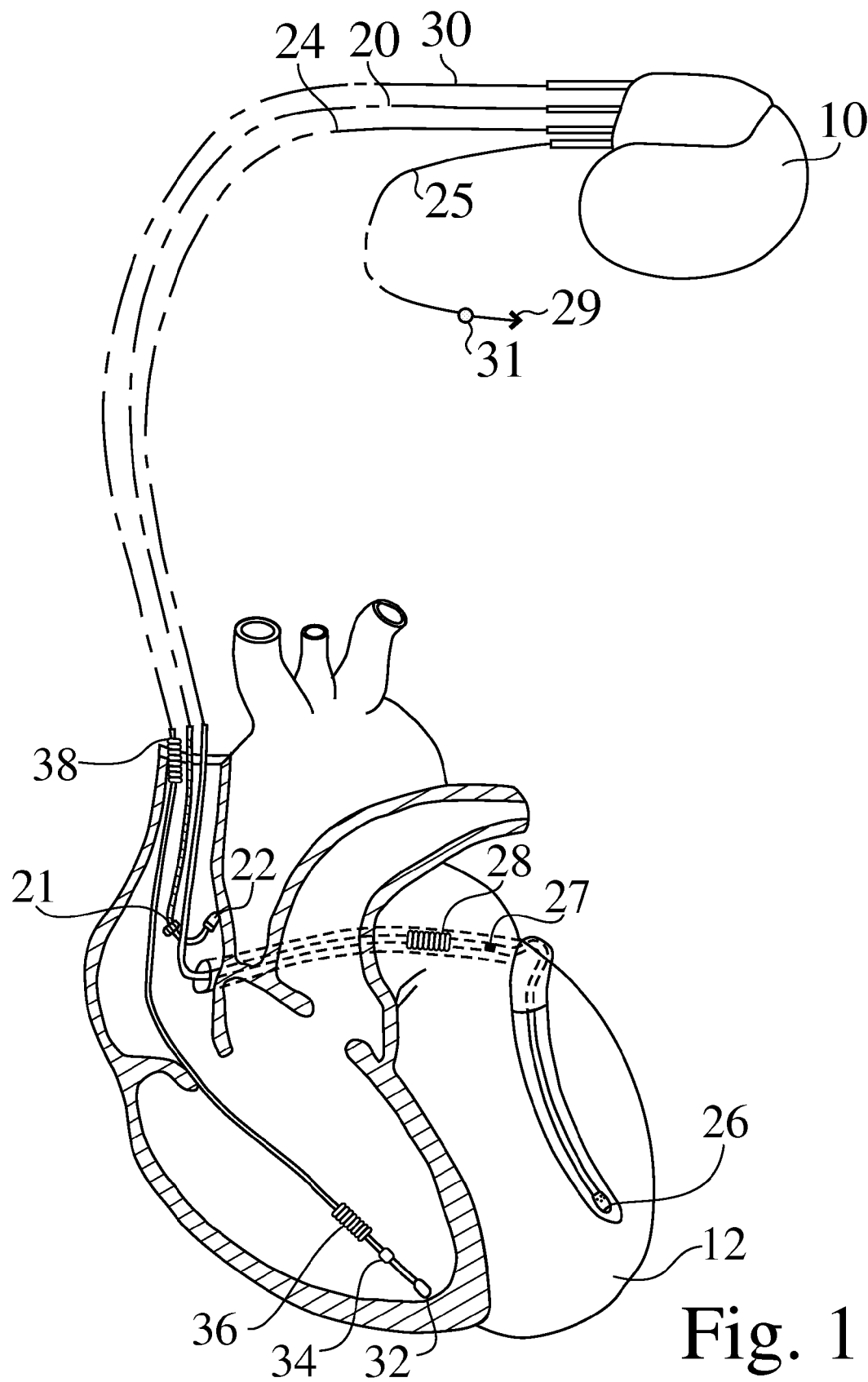
FIG. 1 is a simplified diagram illustrating an implantable stimulation device embodying the present invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial ring electrode 21 and an atrial tip electrode 22, which are typically implanted in the patient's right atrial appendage. The electrodes 21 and 22 form a bipolar electrode pair useful for right atrial pacing and near field targeted atrial activity sensing.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The device 10 includes a still further lead 25. The lead 25 includes a distal electrode 29 and a proximal electrode 31. The electrodes 31 and 29 may be coupled to the vagal nervous system of the patient for applying vagal stimulation therapy when required and as described hereinafter.

Figure 2:
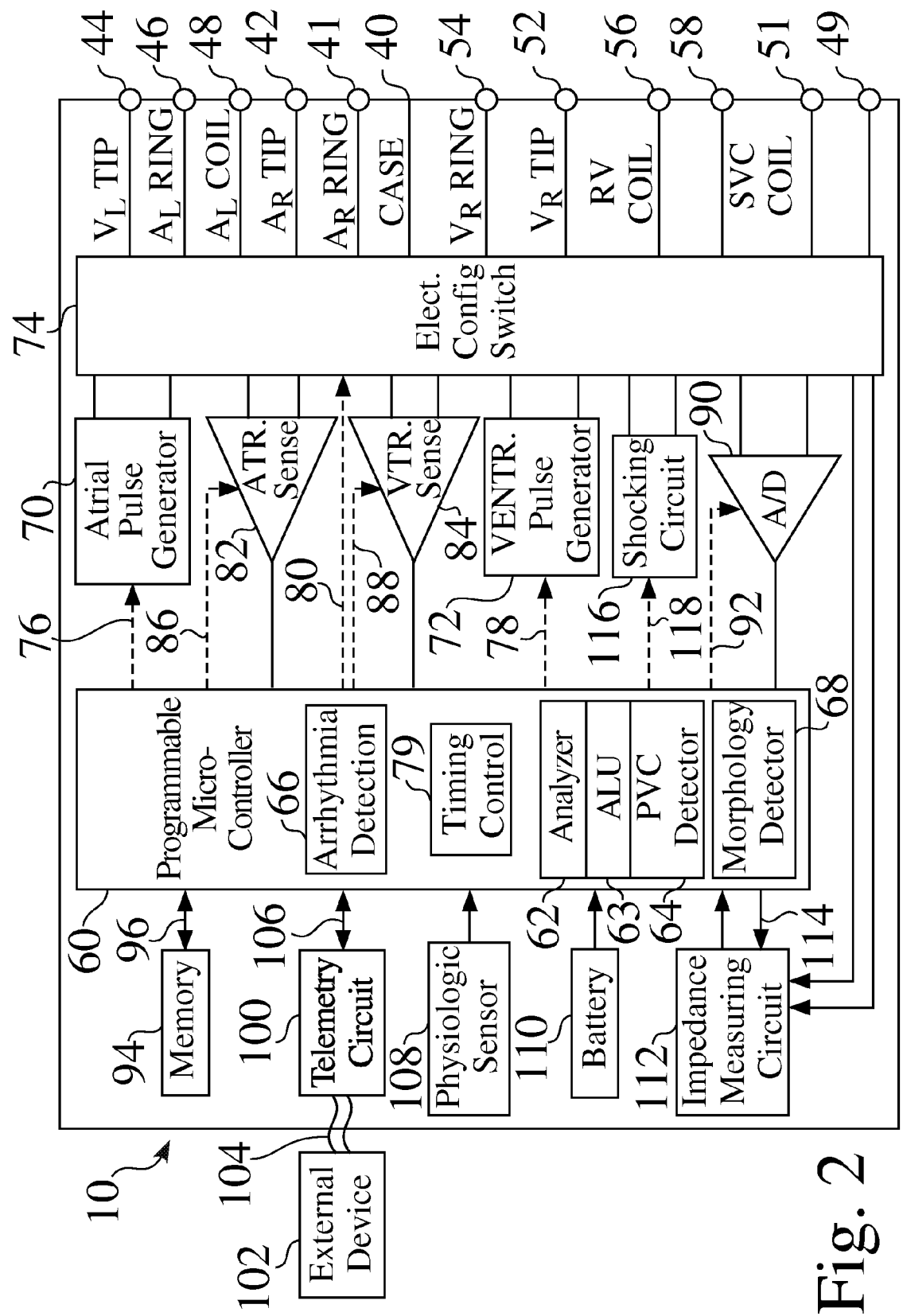
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 47, 48, 49, 52, 54, 56, and 58 (shown schematically and, for convenience, the names of the electrodes to which they are connected are shown next to the terminals). As such, to achieve right atrial sensing and pacing, the connector includes at least a right atrial ring terminal ($A_R$ RING) 41 and a right atrial tip terminal ($A_R$ TIP) 42 adapted for connection to the atrial ring and tip electrodes 21 and 22, respectively.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Lastly, to achieve vagal nerve stimulation, the electrode 31 may be coupled to terminal 51 and the electrode 29 may be coupled to terminal 49.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 includes an arrhythmia detector 66 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 µA), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the implantable cardiac stimulation device 10 has been generally described, this description will now turn to the aspects of the device 10 which more directly relate to this embodiment of the present invention. As previously noted, the present invention is directed to providing a measure of PVC density which may be used to accurately determine a condition of a heart and to control therapy to the heart.

More specifically, this embodiment is directed to an implantable cardiac device which develops a learned PVC density function. The learned PVC density function may then be employed to assess various conditions of a heart and control various therapies and therapy parameters.

To the above end, the device 10 of FIG. 2 is capable of detecting PVCs of the heart. PVCs may be detected, for example, by a PVC detector 64 based upon PR timing of the heart. As previously mentioned, a PVC occurs when a ventricular activation (R waves) without an immediately proceeding corresponding atrial activation (P wave). Hence the lack of PR timing in the heart activity sensed by the atrial sense amplifier 82 and ventricular sense amplifier 84 may be used to detect a PVC. Such a PVC detection method is well known in the art and thoroughly described, for example in U.S. Pat. No. 5,097,832, incorporated herein by reference. This, of course, requires both atrial and ventricular sensing and hence a device having at least dual chamber sensing capability.

Alternatively, PVCs may be detected by analyzing the morphology of a ventricular electrogram. Such an approach is also well known in the art. One such approach is, for example, described in U.S. Pat. No. 5,810,739, also incorporated herein by reference. Morphology PVC detection may be implemented by a morphology detector 68 which analyzes electrograms provided by the data acquisition system 90. The electrograms may be digitized and stored in memory 94. Thereafter, the morphology detector 68 may apply a PVC morphology algorithm to the stored electrograms to detect PVCs. Such detection, as well as the PR timing detection previously described, may be carried out on a beat-by-beat basis.

With the ability to detect PVCs, it is now possible to develop PVC densities, PVC density functions, and learned PVC density functions. A PVC density, as the name implies, is the number of PVCs occurring during a finite time period. Various time periods may be used. However, in this embodiment, time periods of less than an hour are employed because PVC densities are determined on an hourly basis.

To this end, the timing control 79 may be employed to keep track of the various time periods and action times to implement this embodiment. The timing control 79 may therefore be used to time PVC detection intervals and identify when PVC densities are to be developed, when it is time to update data, such as learned PVC density functions, and when it is time to assess a condition of the heart based on the PVC density function and PVC densities or change a therapy.

A PVC density function may be developed by measuring PVC density each hour. The actual PVC detection interval may vary but is preferably less than an hour as, for example, ten minutes. Hence, each hour, for a ten minute period, a PVC density is measured. This provides data points which may then be interpreted by curve smoothing or the like to develop a continuously varying, time dependent PVC density curve or PVC density function. Preferably, the PVC density function extends over a twenty-four hour period to provide a diurnal PVC density function.

A PVC density function may be developed each day and stored in memory 94. After a plurality of such PVC density functions are stored, as for example two PVC density functions, the PVC density functions may be averaged to provide a learned PVC density function. The averaging, and all other mathematical operations required herein may be performed by an arithmetic logic unit (ALU) 63.

Figure 3:
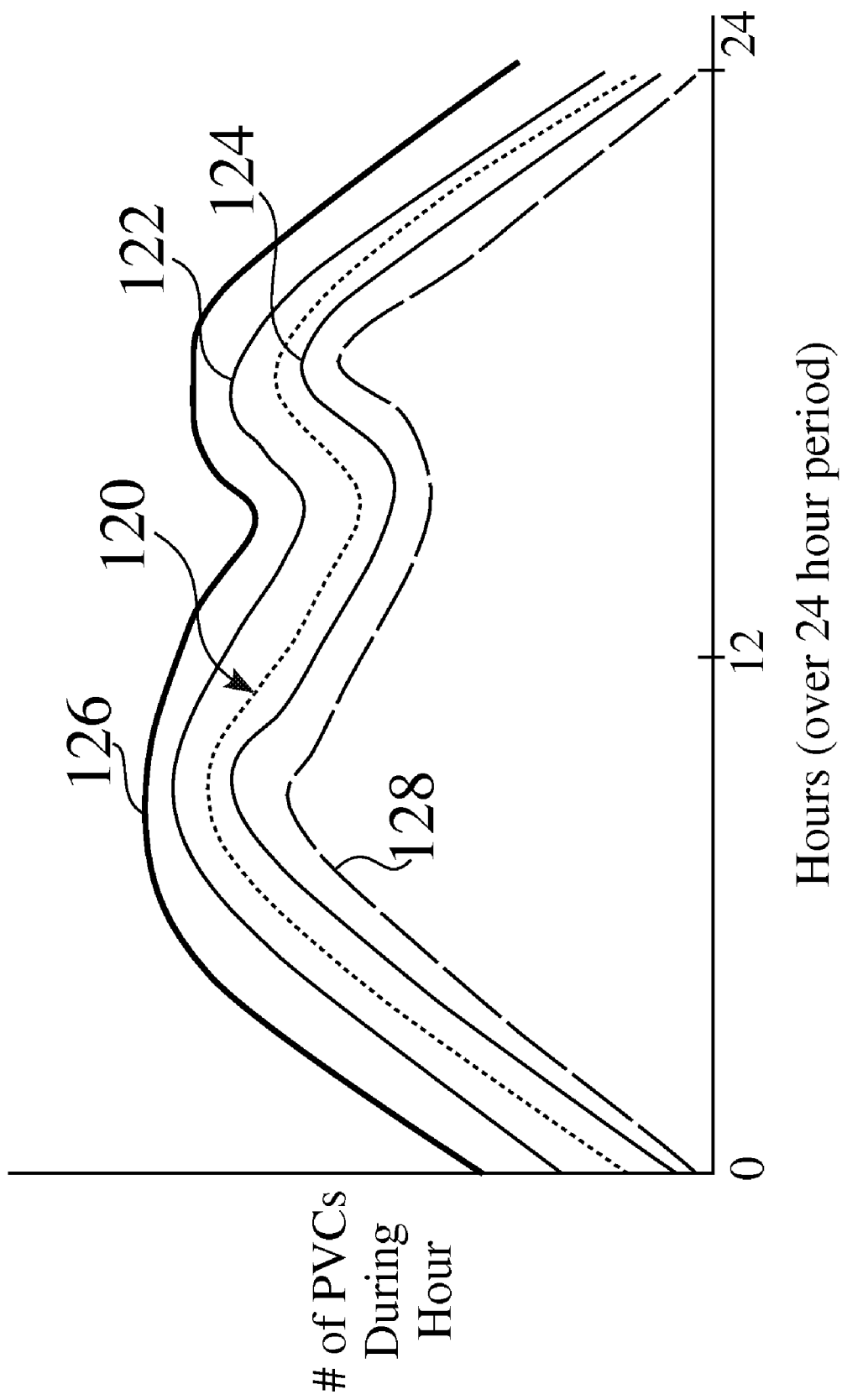
FIG. 3 is a graph illustrating a learned diurnal PVC density function along with corresponding deviations and time varying thresholds.

Such a learned PVC density function is shown in FIG. 3. The learned PVC density function (PVCDF) 120 of FIG. 3 is illustrative only, as learned PVCDFs may take any number of varying shapes. The data used to generate the learned PVCDF 120 may also be used to calculate and plot plus and minus standard deviations 122 and 124 respectively, and upper and lower time varying thresholds 126 and 128. The upper threshold 126 and lower thresholds 128 are hence related to the PVCDF and may, for example, be two standard deviations greater and two standard deviations less than the PVCDF. Other relationships are, of course, possible.

In accordance with this embodiment, the PVCDF 120 may be used to advantage in assessing patient condition. It may further be used for controlling therapy.

As will be seen hereinafter the need for more or less aggressive therapy may be determined and hence controlled. Also, a series of learned PVCDFs, one for each one of a plurality of different pacing rates may be used to select a pacing rate. Still further, the PVCDF 120 may be used to determine when therapy should be regularly applied. Differences in learned PVCDFs developed over time may be used to detect trends in PVC burden or electrical stability (or instability) of the heart and hence whether ventricular arrhythmias are more likely. They may even be used, when compared to diurnal PVCDFs to determine if heart failure has occurred since it has been suggested that like reduced heart rate variability occurring after heart failure, the PVC density variability will also be decreased.

With respect to therapy, such therapy may be, for example, overdrive pacing therapy followed by rate smoothing pacing, to mimic normal sinus rate after a premature ventricular contraction. Such pacing is well known in the art and may be performed by the ventricular pulse generator 72. Alternatively, the therapy may take the form of electrical stimulation of the vagal nervous system utilizing one of the pulse generators 70 or 72 switched to electrodes 31 and 29 of lead 25 by switch 74. Of course, therapies other than those described herein may be employed without departing from the present invention.

Figure 4:
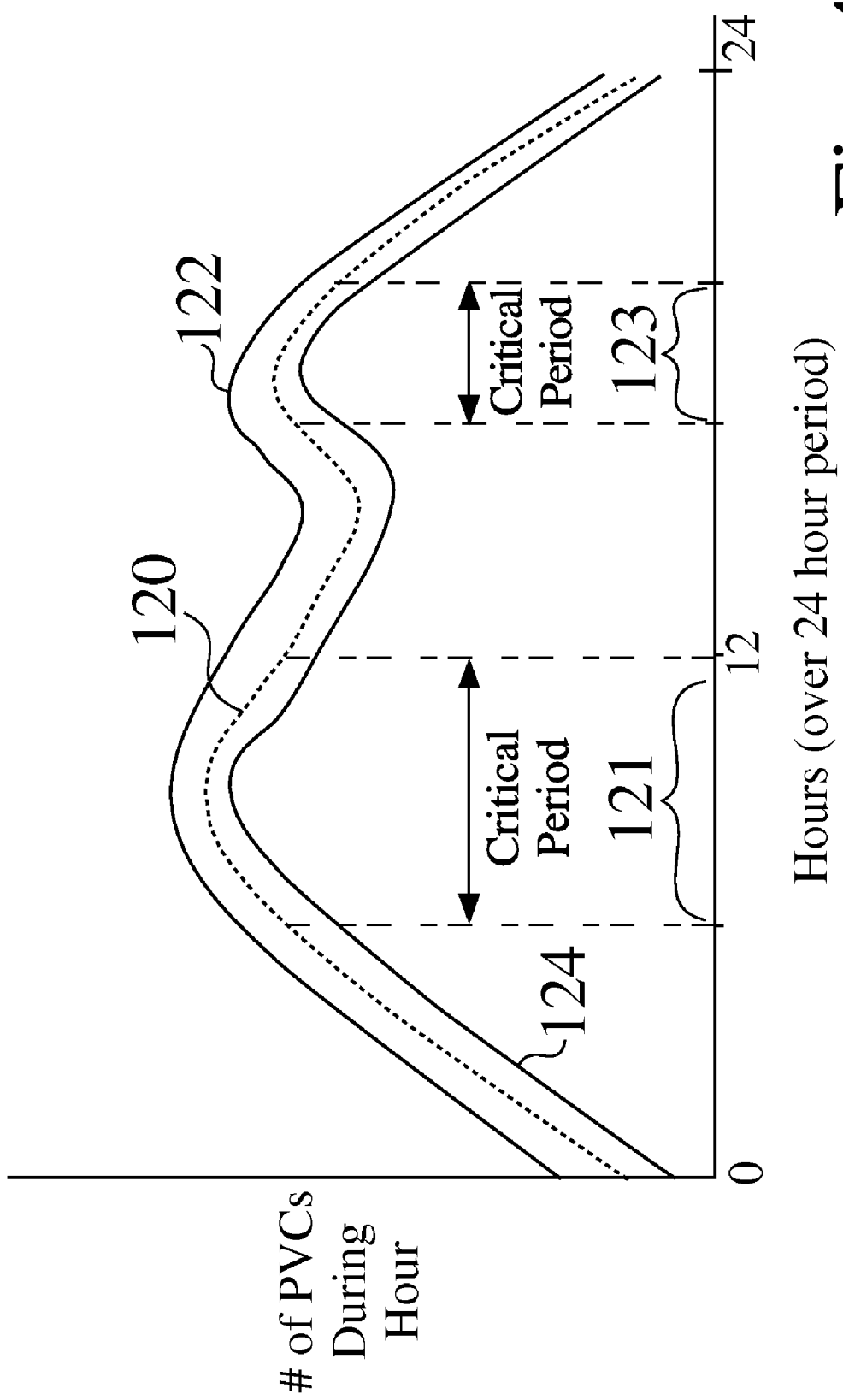
FIG. 4 is a graph of the learned PVC density function of FIG. 3 showing its use for selecting regular therapy times.

Referring now to FIG. 4, it illustrates how the learned PVCDF 120 may be used to advantage to determine when regular therapy should be administered. Here it may be seen that the PVC density maximums may be used to cause therapy to be administered during critical time periods 121 and 123. Further, learned density functions may also be developed for PVC couplet or triplets and their periods of maximum occurrence may also be used to control regularly applied therapy.

Figure 5:
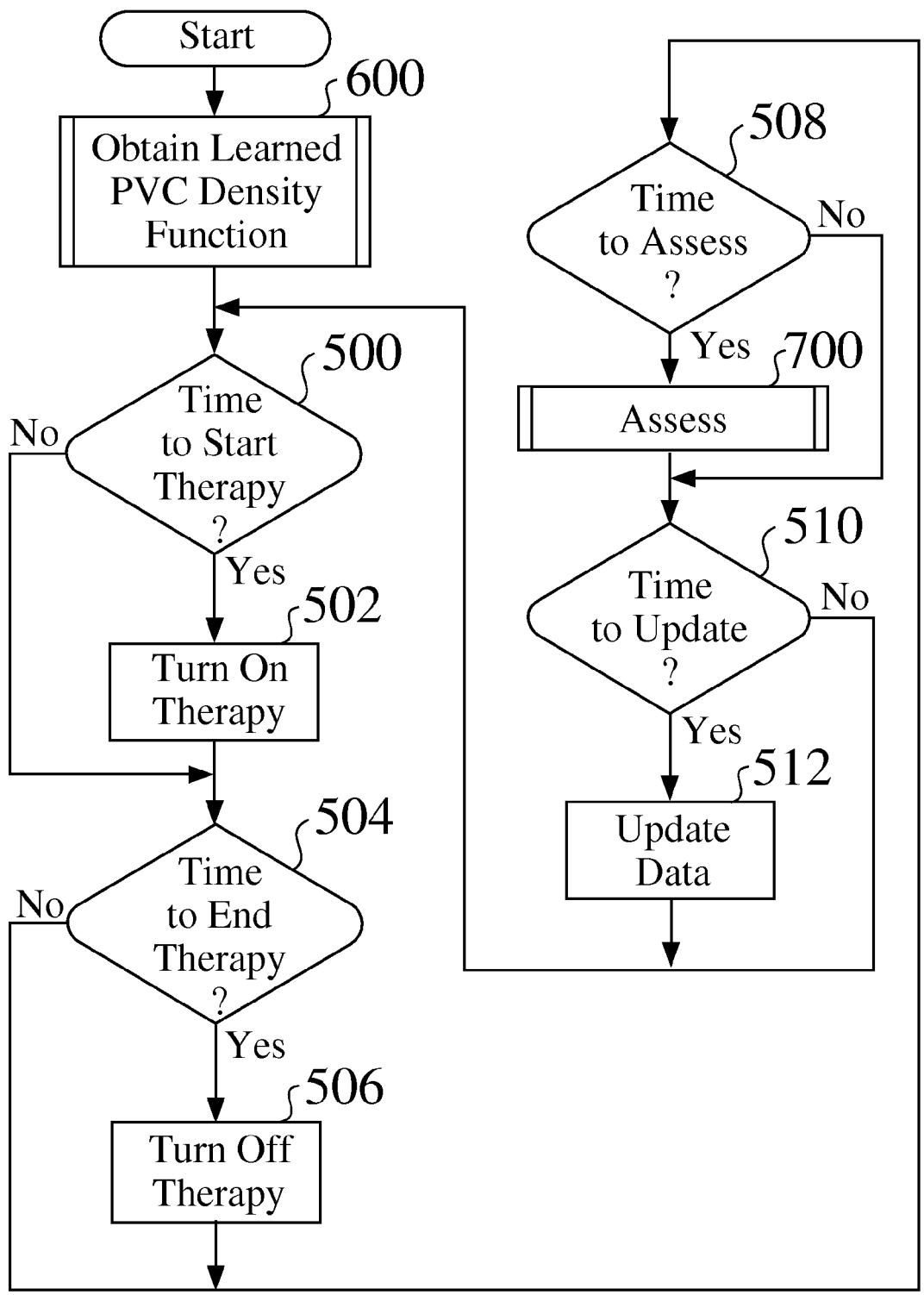
FIG. 5 is a flow chart describing an overview of the operation of one embodiment of the present invention.

In FIG. 5, a flow chart is shown describing an overview of the operation and novel features implemented in one embodiment of the invention. In this flow chart, and the other flow charts herein, the various algorithmic steps are summarized in individual "blocks". Such blocks describe specific actions or decisions that must be made or carried out as the algorithm proceeds. Where a microcontroller (or equivalent) is employed, the flow chart presented herein provide the basis for a "control program" that may be used by such a microcontroller (or equivalent) to effectuate the desired control of the stimulation device. Those skilled in the art may readily write such a control program based on the flow chart and other descriptions presented herein.

The process of FIG. 5 initiates with a subroutine 600 wherein a learned PVC density function is obtained. The subroutine 600 will be described in greater detail hereinafter with reference to FIG. 6. The learned PVC density function developed in subroutine 600 may be similar to the learned PVC density function 120 of FIG. 3 to thereby include plus and minus standard deviations and upper and lower time varying thresholds.

Once subroutine 600 is completed, the process advances to decision block 500 wherein it is determined if it is time to start a regular therapy as, for example, previously described with respect to FIG. 4. If it is time for regular therapy, the process advances to activity block 502 wherein therapy is turned on. If in decision block 500 it is determined that it is not time to start therapy, activity block 502 is bypassed.

The process then advances to decision block 504 wherein it is determined if it is time to end regular therapy. If it is time to end a regular therapy, the process advances to activity block 506 wherein the therapy is terminated. If, in decision block 504, it is determined that it is not time to end regular therapy, activity block 506 is bypassed. The process advances to decision block 508.

In decision block 508, it is determined if it is time to assess a condition of the patient's heart based upon the learned PVC density function or to control a therapy based upon the learned PVC density function. If it is, the process advances to subroutine 700 for assessing the condition of the heart and controlling therapy. The subroutine 700 will be described in greater detail hereinafter with respect to FIG. 7.

If in decision block 508 it is determined that it is not time to assess a condition of the heart or control a therapy based upon the learned PVC density function, or if such assessment and control has been carried out in accordance with subroutine 700, the process advances to decision block 510 wherein it is determined if it is time to update the PVC density data. This decision block may, for example, cause an updated learned PVC density function to be developed. For example, a new learned PVC density function may be developed for any number of a plurality of days and stored in memory 94 to enable trending. For example, a new learned PVC density function may be developed every other day, for example, and the learned PVC density functions may be obtained through interrogation by the external device 102 by activating the telemetry circuit 100. The data update may, of course, be made in other ways as needed or desired. If in decision block 510 it is determined that it is time to update PVC density function data, the process advances to activity block 512 wherein the PVC density function data is updated. The process then returns to decision block 500.

Figure 6:
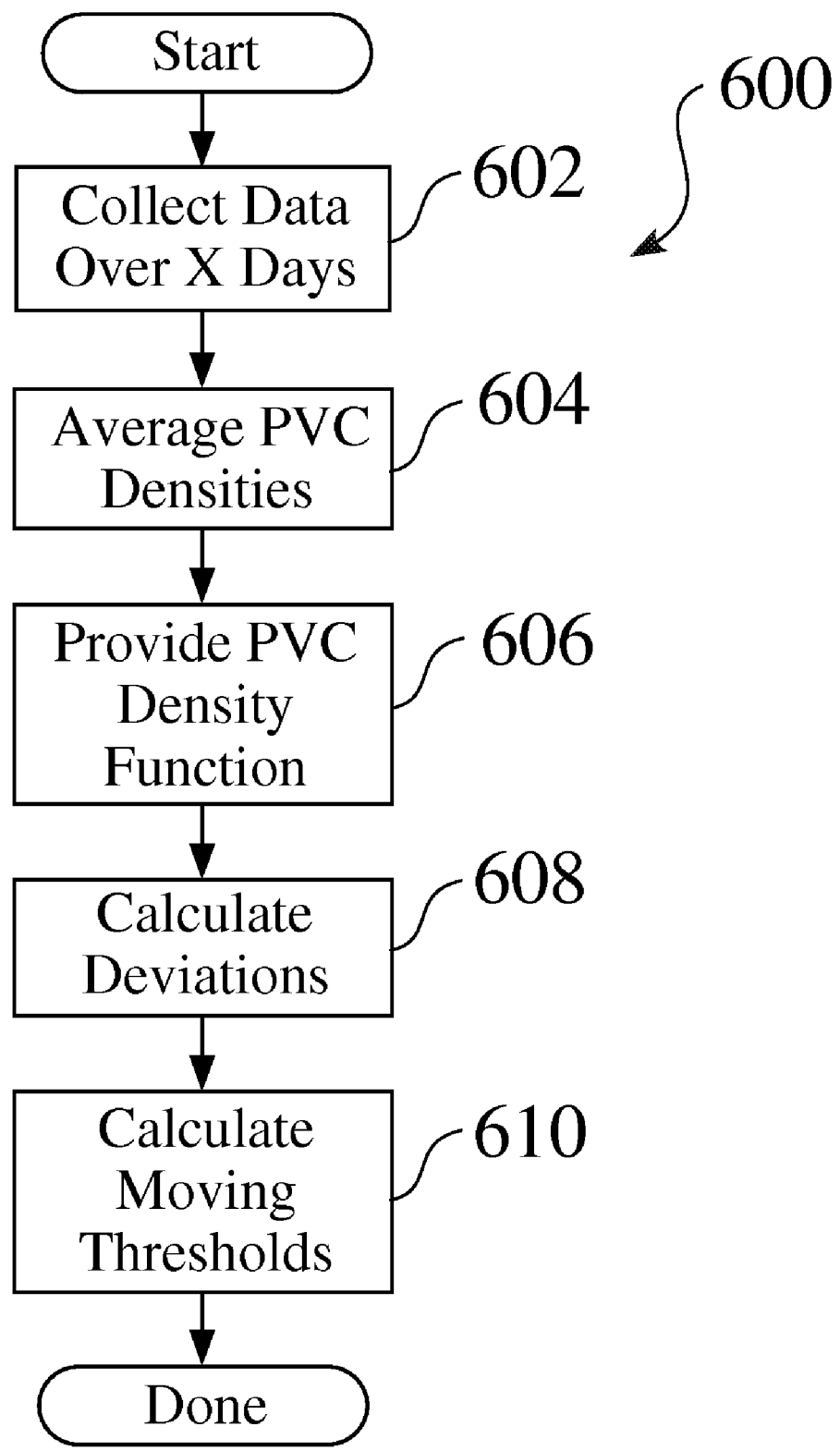
FIG. 6 is a flow chart describing the subroutine of FIG. 5 for obtaining a learned PVC density function.

Referring now to FIG. 6, it describes the subroutine 600 of FIG. 5 wherein learned PVC density function is developed. The process of subroutine 600 initiates with activity block 602 wherein PVC density data is collected over a plurality of days, as for example, two days. As previously described, every hour a new PVC density may be determined by, for example, counting the number of PVCs occurring during a continuous 10 minute period.

Once the data is collected in accordance with activity block 602, the process advances to activity block 604 wherein the PVC density values corresponding in time are averaged. The process then advances to activity block 606 wherein a smoothing curve is applied to the averaged PVC densities to provide a learned diurnal PVC density function such as, for example, the learned diurnal PVC density function 120 of FIG. 3.

The process then advances to activity block 608 wherein the plus and minus standard deviations are calculated. They also may be plotted with the learned diurnal PVC density function as illustrated, for example, as plus and minus standard deviations 122 and 124, respectively, of FIG. 3.

Lastly, in activity block 610 the upper and lower time varying thresholds are calculated. These thresholds, as previously described, are preferably related to the learned PVC density function and may be, for example, twice the plus and minus standard deviations. When plotted, they would appear as the upper moving threshold 126 and the lower moving threshold 128 as illustrated in FIG. 3.

Figure 7:
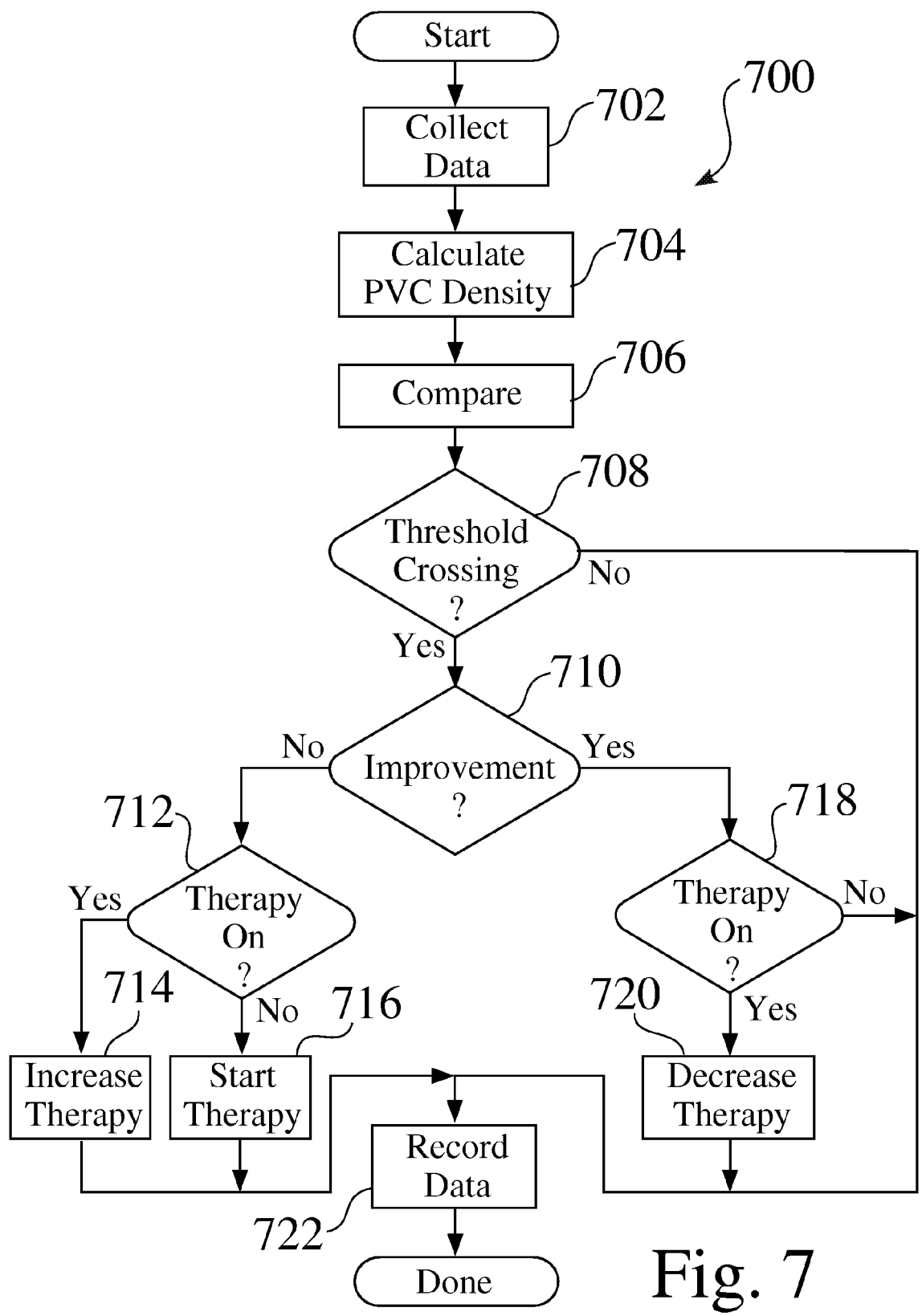
FIG. 7 is a flow diagram describing the assessing subroutine of FIG. 3.

FIG. 7 is a flow diagram describing the subroutine 700 wherein the learned diurnal PVC density function is utilized for analysis and control of therapy. The subroutine 700 is preferably carried out each time a new PVC density is provided and hence may provide for the calculation of a new PVC density on an hourly basis. As a result, the subroutine 700 initiates at activity block 702 wherein data is collected for calculating a PVC density. As previously described, the data calculation may include the counting of the number of PVCs occurring during a finite time period, as for example, 10 minutes. Next, in activity block 704 the PVC density is calculated. Now that the PVC density has been determined, the process advances to activity block 706 wherein the PVC density just calculated is compared to the upper and lower moving thresholds corresponding in time with the PVC density. The comparison may be performed by an analyzer 62 of the device 10 as may be seen in FIG. 2. Once the comparison is made, the process advances to decision block 708 where it is determined if there has been a crossing of the PVC density value of either the upper threshold 126 or the lower threshold 128. If there has not been a crossing, the process advances to activity block 722 wherein the PVC data is recorded for later use in updating the learned diurnal PVC density function or for use in generating a new learned diurnal PVC density function.

If, in decision block 708, it is determined that there has been a crossing in PVC density with either the upper threshold 126 or lower threshold 128, the process advances to decision block 710 wherein it is determined through which threshold the crossing occurred. If there has not been improvement, this signifies that the upper threshold 126 has been crossed. If this is the case, the process advances to decision block 712 wherein it is determined if therapy is currently being applied to the heart. If therapy is currently being applied, the process advances to activity block 714 wherein the aggressiveness of the therapy is increased. If it is determined in decision block 712 that therapy is not currently on, the process then will advance to activity block 716 for initiating therapy. After either activity block 714 or activity block 716, the process advances to activity block 722.

If in decision block 710 it is determined that there is improvement, this signifies that the lower threshold 128 has been crossed. The process then advances to decision block 718 wherein it is determined if therapy is currently on. If therapy is not on, the process immediately advances to activity block 722. However, if therapy is on, the process then advances to activity block 720 wherein the aggressiveness of the applied therapy is decreased.

As may be seen from the foregoing, if the condition of the heart continues to improve, the therapy aggressiveness will continue to be decreased. Contemplated herein is the possibility that the condition will improve enough that in activity block 720, the therapy will be terminated.

Figure 8:
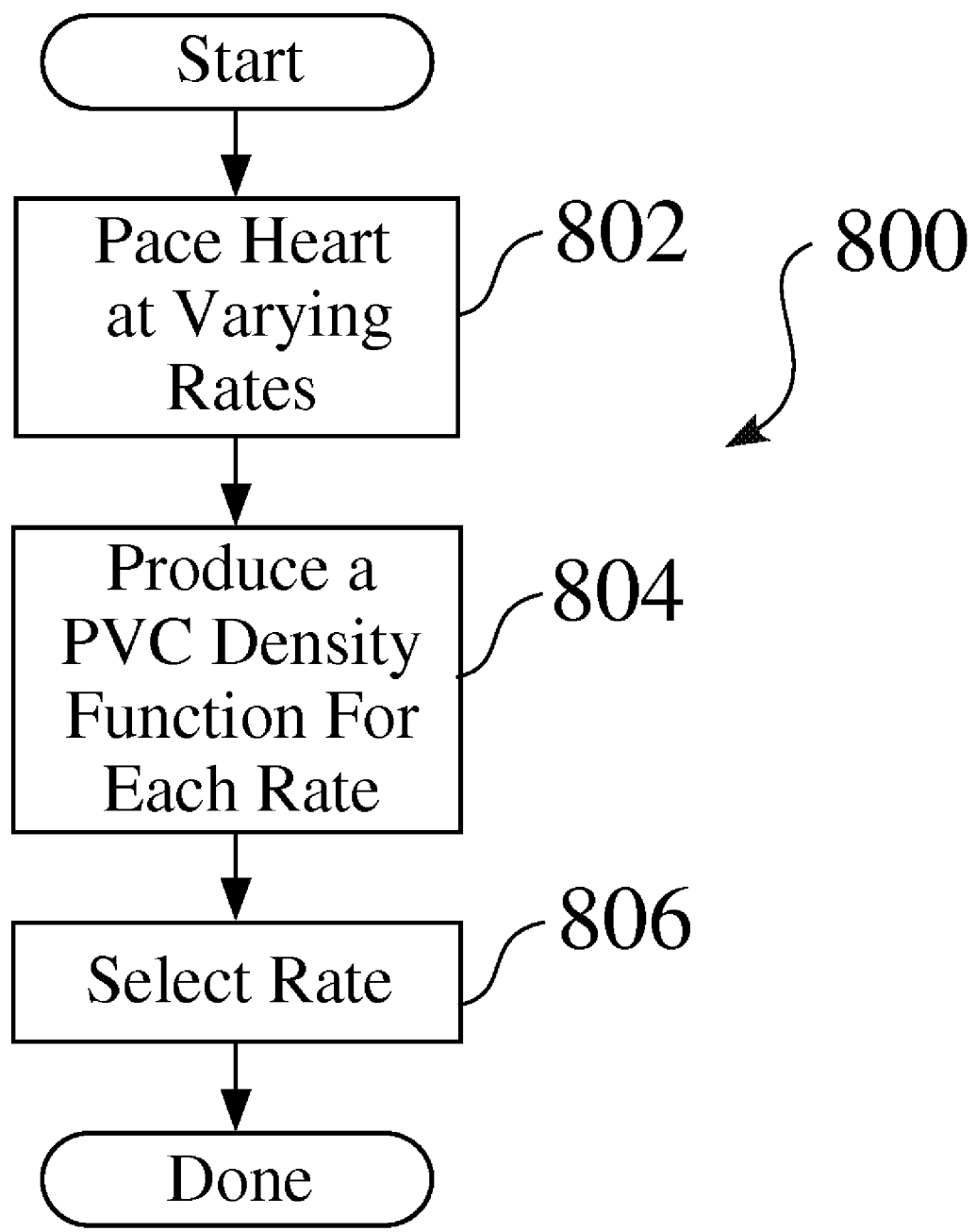
FIG. 8 is a flow diagram describing one embodiment for selecting a pacing rate using learned PVC density functions.

Referring now to FIG. 8, it illustrates a process 100 wherein a pacing rate may be selected for pacing the heart based on a series of learned PVC density functions. Again, the learned PVC density functions may be learned diurnal PVC density functions.

The process initiates with activity block 802 wherein the heart is paced at varying rates. The heart is preferably paced at each one of a plurality of different pacing rates for a period of multiple days, such as two days. During such pacing, PVC densities may be determined on an hourly basis as previously described. When the data has been collected in accordance with activity block 802, the process advances to activity block 804 wherein a learned PVC density function is provided for each pacing rate. As a result, a series of learned PVC density functions will be provided. Once the PVC density functions are determined, the process advances to activity block 806 wherein the pacing rate is selected. The pacing rate selected may be determined by choosing the pacing rate that minimizes one of the total daily PVC density (area under the curve of the diurnal PVC density function), the maximum PVC density as determined from the diurnal PVC density functions, or the pacing rate which results in the least PVC density variability. The process then completes.

In addition to the foregoing, a preventative therapy may be initiated. For example, a change in any one of the above mentioned parameters in selecting the pacing rate may be utilized to indicate the need for preventative therapy.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac device, a method comprising:
applying stimulation pulses to the heart at a plurality of different stimulation rates;
acquiring a plurality of intracardiac electrograms from a heart, at least some of the electrograms including a premature ventricular contraction;
detecting the premature ventricular contractions in the electrograms;
providing a premature ventricular contraction density function for each one of the plurality of different stimulation rates responsive to the detected premature ventricular contractions and deriving an indication of a condition of the heart responsive to the premature ventricular contraction density function.

2. The method of claim 1 wherein the premature ventricular contraction density function is a diurnal premature ventricular contraction density function.

3. The method of claim 1 wherein the providing step includes averaging a plurality of premature ventricular contraction density functions to provide a learned premature ventricular contraction density function for each one of the plurality of different stimulation rates, and wherein the deriving step includes comparing the learned premature ventricular contraction density function to a current premature ventricular contraction density function.

4. The method of claim 1 wherein the providing step includes averaging a plurality of premature ventricular contraction density functions to provide a learned premature ventricular contraction density function for each one of the plurality of different stimulation rates, and wherein the deriving step includes determining a time varying premature ventricular contraction density threshold related to the learned premature ventricular contraction density function, and comparing a current premature ventricular contraction density to the time varying premature ventricular contraction density threshold.

5. The method of claim 1 wherein the providing step includes averaging a plurality of premature ventricular contraction density functions to provide a learned premature ventricular contraction density function for each one of the plurality of different stimulate rates, and wherein the method further comprises the step of selecting a stimulation rate responsive to the learned premature ventricular contraction density functions.

6. The method of claim 1 including the further step of providing regular premature ventricular contraction therapy based upon the premature ventricular contraction density function.

7. The method of claim 1 wherein the providing step includes providing a density function of at least one of premature ventricular contraction couplets, premature ventricular contraction triplets, and premature ventricular contractions with coupling intervals less than a predetermined coupling interval.

8. The method of claim 1 wherein the providing step includes providing a learned premature ventricular contraction density function for each one of the plurality of different stimulate rates, and wherein the method further comprises the step of selecting a stimulation rate responsive to the learned premature ventricular contraction density functions.

9. An implantable cardiac device comprising:
a pulse generator that provides stimulation pulses to a heart at different stimulation rates;
a sensor that acquires a plurality of intracardiac electrograms from the heart, at least some of the electrograms including a premature ventricular contraction;
a detector that detects the premature ventricular contractions in the electrograms;
a processor that provides a premature ventricular contraction density function responsive to the detected premature ventricular contractions to provide a learned premature ventricular contraction density function for each one of a plurality of different stimulation rates; and
an analyzer that derives an indication of a condition of the heart responsive to the premature ventricular contraction density function and selects a stimulation rate responsive to the learned premature ventricular contraction density function.

10. The device of claim 9 wherein the processor averages the plurality of premature ventricular contraction density functions to provide the learned premature ventricular contraction density function, and wherein the analyzer compares the learned premature ventricular contraction density function to a current premature ventricular contraction density function.

11. The device of claim 10 wherein the condition is electrical stability of the heart.

12. The device of claim 10 wherein the condition is premature ventricular contraction daily frequency.

13. The device of claim 10 wherein the learned premature ventricular contraction density function is a learned diurnal premature ventricular contraction density function and wherein the current premature ventricular contraction density function is a diurnal premature ventricular contraction density function.

14. The device of claim 9 wherein the processor averages a plurality of premature ventricular contraction density functions to provide the learned premature ventricular contraction density function, wherein the processor determines a time varying premature ventricular contraction density threshold related to the learned premature ventricular contraction density function, and wherein the analyzer compares a current premature ventricular contraction density to the time varying premature ventricular contraction density threshold.

15. The device of claim 14 wherein the analyzer controls a premature ventricular contraction therapy responsive to the comparison of the current premature ventricular contraction density to the time varying threshold.

16. The device of claim 9 wherein the premature ventricular contraction density functions are diurnal density functions.

17. The device of claim 9 wherein the analyzer selects the stimulation rate corresponding to a learned premature ventricular contraction density function having a smallest maximum premature ventricular contraction density function metric.

18. The device of claim 9 wherein the analyzer selects the stimulation rate corresponding to a learned premature ventricular contraction density function having a least total daily premature ventricular contraction density.

19. The device of claim 9 wherein the analyzer selects the stimulation rate corresponding to a learned premature ventricular contraction density function having a least premature ventricular contraction density.

20. The device of claim 9 wherein the analyzer selects the stimulation rate corresponding to a learned premature ventricular contraction density function having a least premature ventricular contraction density variability.

21. The device of claim 17 wherein the premature ventricular contraction density functions are diurnal premature ventricular contraction density functions.

22. The device of claim 17 further comprising a premature ventricular contraction therapy circuit including the pulse generator and wherein the analyzer enables the therapy circuit responsive to a change in the premature ventricular contraction density function metric.

23. The device of claim 9 further comprising a premature ventricular contraction therapy circuit that provides premature ventricular contraction therapy and wherein the therapy circuit provides regular premature ventricular contraction therapy based upon the premature ventricular contraction density function.

24. The device of claim 23 wherein the detector further detects premature ventricular contraction complexes and wherein the therapy circuit provides therapy responsive to detection of a premature ventricular contraction complex density above a predetermined density.

25. The device of claim 24 wherein the premature ventricular contraction complexes include at least one of premature ventricular contraction couplets, and premature ventricular contraction triplets.

26. The device of claim 9 wherein the processor further provides a density function of at least one of premature ventricular contraction couplets, premature ventricular contraction triplets, and premature ventricular contractions with coupling intervals less than a predetermined coupling interval.

27. An implantable cardiac device comprising:
- a pulse generator that provides stimulation pulses to a heart at different stimulation rates;
- a sensor that acquires a plurality of intracardiac electrograms from the heart, at least some of the electrograms including a premature ventricular contraction;
- a detector that detects the premature ventricular contractions in the electrograms;
- a processor that provides a diurnal premature ventricular contraction density function responsive to the detected premature ventricular contractions and the different stimulation rates;
- a therapy circuit that provides premature ventricular contraction therapy; and
- an analyzer that controls the therapy circuit responsive to the diurnal premature ventricular contraction density function.

28. An implantable cardiac device comprising:
- a pulse generator that provides stimulation pulses to a heart at different stimulation rates;
- a sensor that acquires a plurality of intracardiac electrograms from the heart, at least some of the electrograms including a premature ventricular contraction;
- a detector that detects the premature ventricular contractions in the electrograms;
- a processor that provides a learned diurnal premature ventricular contraction density function responsive to the detected premature ventricular contractions for each one of a plurality of different stimulation rates; and
- an analyzer that derives an indication of a condition of the heart responsive to the learned diurnal premature ventricular contraction density function and selects a stimulation rate responsive to the learned premature ventricular contraction density function.

* * * * *